(12) United States Patent
Butz et al.

(10) Patent No.: US 9,968,426 B2
(45) Date of Patent: May 15, 2018

(54) METHOD FOR THE PRODUCTION OF AN INTERDENTAL CLEANER

(71) Applicant: INTERBROS GMBH, Schönau (DE)

(72) Inventors: Jürgen Butz, Schönau (DE); Gerhard Pötsch, Freiburg (DE)

(73) Assignee: INTERBROS GMBH, Schönau (DE)

( * ) Notice: Subject to any disclaimer, the term of this patent is extended or adjusted under 35 U.S.C. 154(b) by 197 days.

(21) Appl. No.: 14/901,162

(22) PCT Filed: Jun. 23, 2014

(86) PCT No.: PCT/EP2014/001698
§ 371 (c)(1),
(2) Date: Dec. 28, 2015

(87) PCT Pub. No.: WO2014/206547
PCT Pub. Date: Dec. 31, 2014

(65) Prior Publication Data
US 2016/0135932 A1    May 19, 2016

(30) Foreign Application Priority Data

Jun. 28, 2013 (DE) .................. 10 2013 010 782

(51) Int. Cl.
*A61C 15/02* (2006.01)
*A46B 3/00* (2006.01)
*A46D 3/00* (2006.01)
*A61C 15/00* (2006.01)
*A46B 3/18* (2006.01)

(52) U.S. Cl.
CPC .............. *A61C 15/02* (2013.01); *A46B 3/005* (2013.01); *A46D 3/00* (2013.01); *A61C 15/00* (2013.01); *A46B 3/18* (2013.01); *A46B 2200/108* (2013.01)

(58) Field of Classification Search
CPC ......... A61C 15/02; A61C 15/00; A46B 3/005; A46B 3/18; A46D 3/00
See application file for complete search history.

(56) References Cited

U.S. PATENT DOCUMENTS

| 2,580,378 | A | * | 12/1951 | Peterson | ................. A46D 3/05 15/206 |
|---|---|---|---|---|---|
| 5,123,841 | A | | 6/1992 | Millner | |
| 6,902,399 | B2 | | 6/2005 | Mannschedel | |
| 7,975,345 | B2 | | 7/2011 | Weber | |
| 9,173,479 | B2 | | 11/2015 | Butz et al. | |
| 2002/0172922 | A1 | | 11/2002 | Mannschedel | |
| 2006/0174910 | A1 | | 8/2006 | Coopersmith | |
| 2007/0111158 | A1 | | 5/2007 | Han et al. | |
| 2008/0313834 | A1 | | 12/2008 | Weber | |

(Continued)

FOREIGN PATENT DOCUMENTS

| AT | 503 725 B1 | 11/2008 |
|---|---|---|
| DE | 101 23 814 A1 | 12/2002 |

(Continued)

*Primary Examiner* — Shay Karls
(74) *Attorney, Agent, or Firm* — McGlew and Tuttle, P.C.

(57) ABSTRACT

An interdental cleaner has a rod-shaped carrier formed of plastic, which has a structuring with structural elements radially protruding from the carrier on at least one section of an axial length thereof. The carrier is twisted in at least one part of the section having the structuring together with the structuring about a carrier longitudinal axis.

13 Claims, 13 Drawing Sheets

(56) References Cited

U.S. PATENT DOCUMENTS

2014/0158152 A1   6/2014  Butz et al.
2014/0295378 A1  10/2014  Lyngstadaas et al.
2015/0257523 A1   9/2015  Butz et al.

FOREIGN PATENT DOCUMENTS

| DE | 10 2011 011 323 A1 | 8/2012 |
| DE | 10 2011 101391 A1 | 11/2012 |
| EP | 0 932 371 A1 | 8/1999 |
| EP | 1 679 017 A1 | 7/2006 |
| WO | 98/16169 A1 | 4/1998 |
| WO | 2013/072308 A2 | 5/2013 |
| WO | 2014/023395 A1 | 2/2014 |

* cited by examiner

METHOD FOR THE PRODUCTION OF AN INTERDENTAL CLEANER

CROSS REFERENCE TO RELATED APPLICATIONS

This application is a United States National Phase Application of International Application PCT/EP2014/001698 filed Jun. 23, 2014 and claims the benefit of priority under 35 U.S.C. § 119 of German Patent Application 10 2013 010 782.2 filed Jun. 28, 2013 the entire contents of which are incorporated herein by reference.

FIELD OF THE INVENTION

The present invention pertains to an interdental cleaner with a rod-shaped carrier consisting of plastic, which has a structuring with structural elements radially protruding from the carrier at least on a section of its axial length. The present invention pertains, furthermore, to a method for manufacturing an interdental cleaner, wherein a rod-shaped carrier consisting of plastic is provided with a structuring with structural elements radially protruding from the carrier on at least a section of its axial length.

BACKGROUND OF THE INVENTION

Besides the older interdental cleaners consisting of wood or metal wire, interdental cleaners consisting of plastic are nowadays known, as they are shown and described in EP 0 932 371 A1. Such an interdental cleaner has a rod-shaped carrier consisting of a first, relatively hard and dimensionally stable plastic, which is provided in the front area of its axial length with a coating consisting of a second, soft plastic, for example, a thermoplastic elastomer. On its radially outer side, the coating may have a structuring in the form of knobs or radially outwardly extending fingers in order to increase the cleaning action. The user can grasp the interdental cleaner on a grip section of the rod-shaped carrier and insert the rod-shaped carrier with the coating carrying the structuring into an interdental space and move it there to and fro, as a result of which the interdental space is cleaned and possibly adhering particles are loosened.

It was found that it is advantageous for the cleaning action to be achieved with the interdental cleaner if the deformability of the interdental cleaner is high enough, on the one hand, to clean even difficult-to-reach sections of the interdental space, and, on the other hand, the interdental cleaner must be sufficiently flexurally rigid in order to be able to adequately penetrate into small interdental spaces. Since each user imposes different requirements in this respect on an interdental cleaner, it would be desirable per se to market interdental cleaners with different deformabilities and flexural rigidities. It is, however, necessary for this to keep different injection molds in stock and/or to use different plastic materials and/or to manufacture different geometries of the interdental cleaner. In any case, this is associated with considerable additional costs.

SUMMARY OF THE INVENTION

A basic object of the present invention is to create an interdental cleaner, which has a good cleaning action and can be manufactured during its manufacture with different rigidities and with different deformation properties.

Moreover, a method is provided, with which a corresponding interdental cleaner can be manufactured in a simple manner.

The object is accomplished according to the present invention by an interdental cleaner having a carrier that is twisted about a longitudinal axis together with at least a part of a section having structuring. Due to the twisting, the rod-shaped carrier becomes compacted and deformed in its longitudinal direction, as a result of which the spatial stability of the carrier and hence also the deformation properties there will change. It is thus possible to affect and set the deformation properties of the interdental cleaner according to the present invention solely by the extent of twisting, without changing the material or a changed geometry of the injection mold being necessary.

The twisting of the rod-shaped carrier, together with the structuring, brings with it the further advantage that the structuring is distributed over the circumference because of the twisting. Structural elements that are arranged at first only in a linear row extending in the longitudinal direction of the interdental cleaner can also be arranged subsequently over the circumference of the interdental cleaner, as a result of which they make a better contribution to the cleaning action.

Provisions may be made in a possible embodiment of the present invention for the structuring to have radially protruding fingers and/or lips. The fingers and/or lips may be formed integrally in one piece on a coating of the carrier, which is, for example, a sleeve-like coating. The carrier preferably consists of a first, relatively hard plastic material and is surrounded in a part of its axial length with the, for example, sleeve-like coating consisting of a relatively soft second plastic material, for example, a thermoplastic or duroplastic elastomer, silicone or another soft plastic, said coating being formed on the outside in one piece with the radially outwardly protruding fingers and/or lips.

In addition or as an alternative hereto, provisions may be made for the structuring to have radially protruding bristles, which are preferably arranged in at least one row. The bristles may be arranged in one or two straight rows, which are arranged on opposite sides of the rod-shaped carrier and extend in the longitudinal direction of the carrier and may then be deformed by the twisting such that the at least one row or rows extends/extend helically around the carrier.

The bristles are preferably held securely in the carrier consisting of plastic and/or embedded in the coating and held securely as a result.

In the sense of the present application, bristles are thin prefabricated sections of a monofilament or multifilament consisting of plastic, the bristles having a maximum diameter of 0.25 mm and may be used as individual bristles and/or as a bundle of bristles.

The term "axial" used in this text pertains to the longitudinal axis of the rod-shaped carrier and optionally also to the longitudinal axis of a coating. The term "radial" correspondingly pertains to a direction extending at right angles to the axial longitudinal direction.

The fingers and/or lips and/or bristles may extend either radially, i.e., at right angles to the longitudinal axis of the interdental cleaner, or also obliquely thereto, i.e., with a radial component, which is also covered by the term "radial."

The twisting of the carrier leads to a twisting of the structuring about the longitudinal axis of the interdental cleaner. After the torsional force twisting the carrier no longer acts, the carrier usually springs back because of its elastic properties by a small amount against the direction of twisting, while it maintains a permanent torsional deformation or twisting. Provisions are preferably made for the permanent torsional deformation to lead to a twisting of the structuring over an angle of >30°, especially in the range of 60° to 360°, especially in the range of 60° to 120° and especially preferably 90°±20°.

Twisting by 10 to 50 revolutions per m, preferably a twisting by 10 to 40 revolutions per meter and especially a twisting by about 15 to 20 revolutions per meter may also be provided.

A further adaptation of the deformation properties of the rod-shaped carrier and hence of the interdental cleaner can be achieved by arranging a reinforcing insert, which preferably has a higher flexural rigidity than the carrier, so that the interdental cleaner is more rigid in its entirety, in the carrier in at least some sections.

Provisions may be made in a possible embodiment of the present invention for the reinforcing insert to be formed by at least one wire, especially a metal wire or a plastic wire, which extends axially in the longitudinal direction of the carrier. Provisions may be made in a variant for two wires extending in parallel to be arranged and connected to one another at their front ends, forming a U-shaped transition area. Bristles may be arranged and held between the wires.

In respect to the method, the above-mentioned object is accomplished according to the present invention by the carrier to be twisted in at least one part of the section having the structuring together with the structuring about its longitudinal axis. Provisions may be made for this, for example, for the carrier to be grasped in two areas located axially at spaced locations from one another by means of holding devices, for example, clamping jaws, and preferably to be clamped firmly and for the holding devices to be subsequently twisted relative to one another, as a result of which the carrier is twisted about its longitudinal axis. The holding devices are subsequently opened, as a result of which the carrier is released from the clamped holding and can spring back to a certain extent, but it remains twisted.

Provisions may be made in a variant of the method according to the present invention for the mutual distance between the holding devices to be changed and especially increased during the twisting. The change or increase in the distance between the holding devices during the twisting may take place either stepwise or preferably continuously. The holding forces and the torsional forces are prevented in this manner from being always introduced at the same point of the carrier or coating.

Provisions are made in a preferred embodiment of the present invention for one of the holding devices to be stationary, while the other holding device is displaced axially in the direction of the tip of the interdental cleaner during the twisting, and the holding and clamping forces are selected to be such that the displacement of the holding device will not preferably lead to a stretching of the carrier, i.e., no excessive axial tensile forces are introduced into the carrier.

Provisions may be made in a variant of the present invention for the carrier to be heated before and/or during the twisting. It is possible in this manner to reduce the rigidity of the plastic material of the carrier and of a coating that may be present and thus to modify the resilient properties of the material and to adapt them in a desired manner.

The twisting of the carrier leads to a permanent twisting of the structuring about the longitudinal axis of the interdental cleaner. Provisions are made in a preferred embodiment for the permanent twisting of the structuring to extend over an angle of >30°, especially in the range of 60° to 360° and especially in the range of 60° to 120°. A permanent twisting of the structuring by 90°±20° is especially preferred.

The carrier is preferably provided prior to the twisting in the areas of the structuring with a sleeve-like structuring, which carries the structural elements of the structuring either in an at least partially embedded form and/or on its outer side. Provisions may be made in this connection for the structuring to have radially protruding fingers and/or lips, which are made integrally in one piece with and on the coating. As an alternative or in addition hereto, provisions may be made for the structuring to have radially protruding bristles, which are embedded in the carrier and/or in the coating.

It is possible, as an alternative, to twist a rod-shaped spring steel in advance and to fix it in this twisted position. The spring steel is then enclosed with the plastic forming the carrier and optionally also with the plastic forming the coating and especially extrusion-coated. The fixation of the twisted spring steel is then abolished, so that this will spring back and resume its original configuration in the ideal case. The carrier and the structuring located on it are twisted during this springing back.

The bristles may be arranged on and in the interdental cleaner in a possible embodiment of the present invention by the bristles being positioned, located next to each other in one plane, in an injection mold together with the carrier. The carrier may either already be prefabricated or it may have been formed in the injection mold in an immediately preceding method step. The bristles and the carrier are spray-coated in the injection mold with a soft plastic, for example, a thermoplastic elastomer, so that the bristles are held securely in the coating and radially protrude from same. The protruding ends of the bristles are then cut to a desired length, after which the carrier with the coating and with the bristles and possibly with the fingers and/or lips formed integrally in one piece on the outer side of the coating is twisted about the longitudinal axis of the carrier in the above-mentioned manner.

Provisions may be made in an alternative embodiment of the method for the bristles to be inserted, located in one plane, into an injection mold and to be subsequently extrusion-coated with the plastic forming the carrier and to be embedded in this. The carrier holding the bristles is subsequently preferably partially extrusion-coated with the plastic forming the coating, the bristles radially protruding from the coating. The bristles are subsequently cut to a desired dimension, after which the twisting is carried out in the aforementioned manner. The bristles may be cut in the still closed mold or during the opening of the mold or with the mold opened or also outside the mold in a separate cutting station.

A reinforcing insert, which may be, for example, a wire extending axially in the longitudinal direction of the carrier, especially metal wire or plastic wire, may be incorporated in the carrier in advance. If the carrier is also arranged in the area of the structuring within the carrier, it is twisted together with the carrier in this area.

The wire may be a one-layer or double-layer wire. If the wire is arranged in a double layer, it is possible to arrange and especially clamp bristles between the layers and to securely preposition them hereby before the wire and the bristles are extrusion-coated with the plastic material of the carrier.

Further details and features of the present invention can be found in the following description of an exemplary embodiment with reference to the drawings.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 17 is an alternative embodiment of the front, twisted end of the interdental cleaner;

DESCRIPTION OF THE PREFERRED EMBODIMENTS

Figure 1:
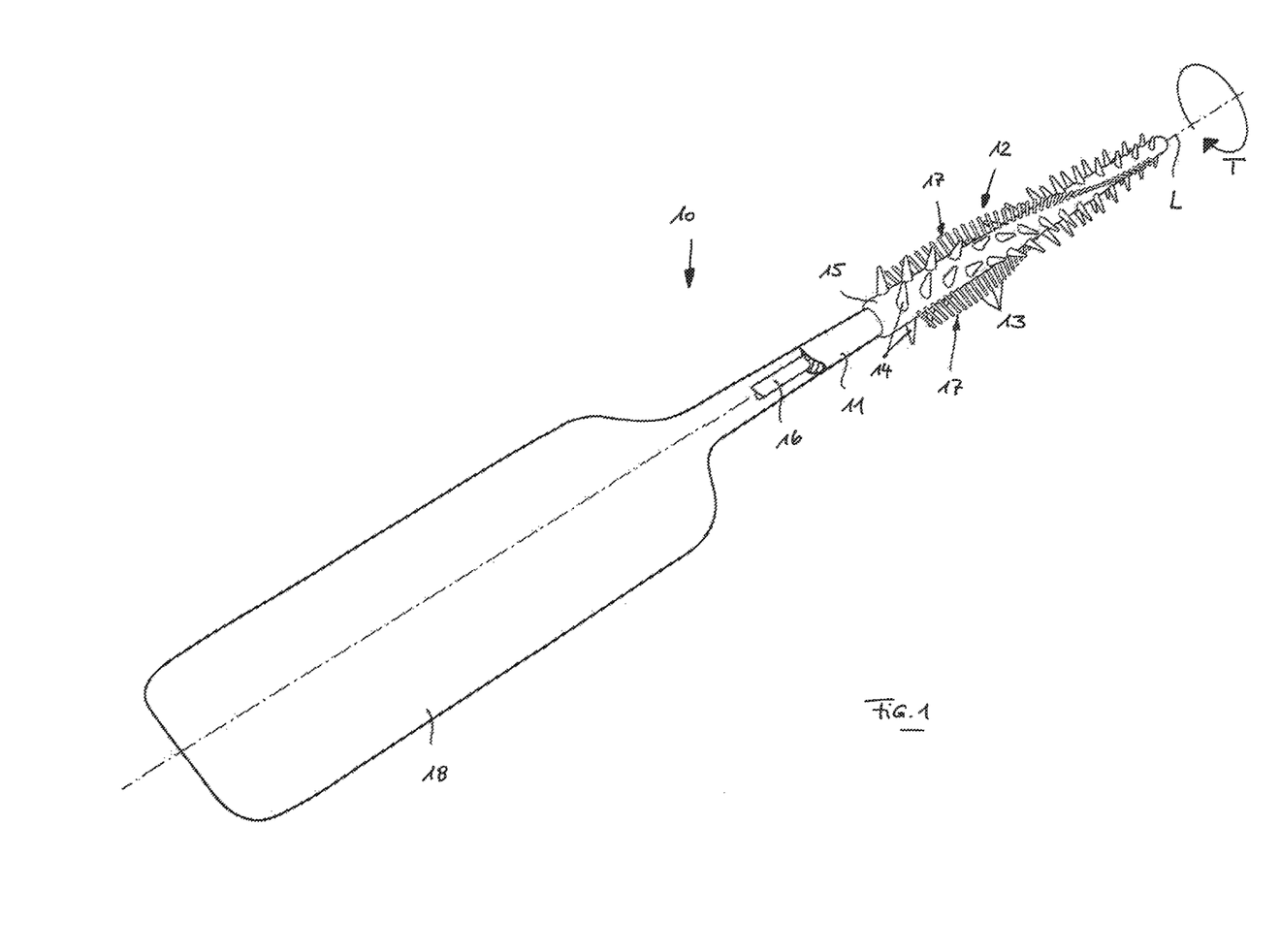
FIG. 1 is a perspective view of an interdental cleaner according to the present invention.

FIG. 1 shows a perspective view of an interdental cleaner 10 according to the present invention, which has a rod-shaped carrier 11. The carrier 11 has an axial longitudinal axis L and preferably consists of a hard or dimensionally stable first plastic material.

The carrier 11 has a structuring 12 in its end area that is the right-hand end area according to FIG. 1 and a grip part 18, by which a user can grasp the interdental cleaner 10, at its opposite end, which is the left-hand end according to FIG. 1.

The structuring 12 is formed by a sleeve-like coating 15 consisting of a soft second plastic material, especially a thermoplastic elastomer, said coating 15 having on its outer side radially outwardly protruding fingers 14 formed integrally in one piece. Furthermore, bristles 13, which protrude radially outwardly and extend in two rows 17 in the longitudinal direction of the carrier 11 and extend helically around the carrier 11, are embedded in the coating 15. The two bristle rows 17 are arranged each diametrically opposite on the coating 15, and they are coiled by half a revolution, i.e., about 180°, in the longitudinal direction of the coating 15 in the exemplary embodiment being shown.

A first method for manufacturing the interdental cleaner according to the present invention will be explained below on the basis of FIGS. 2 through 9.

Figures 2, 3:
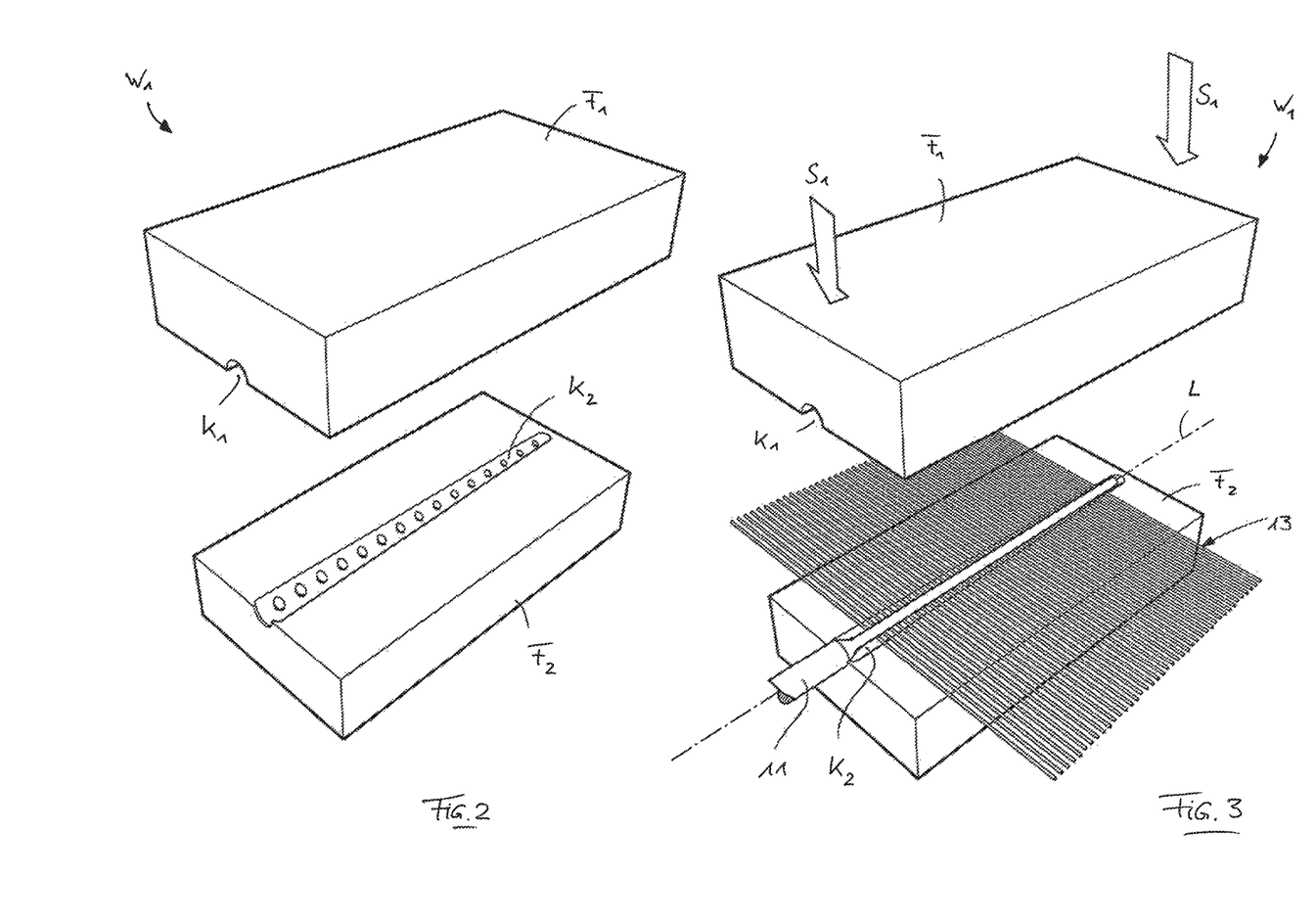
FIG. 2 is a perspective view of an opened injection mold.
FIG. 3 is a view showing the injection mold according to FIG. 2 after insertion of the carrier and of the bristles.

FIG. 2 shows a schematic view of an opened injection mold W with an upper mold half $F_1$, which has an upper cavity $K_1$, and a lower mold half $F_2$, which has a lower cavity $K_2$.

Figure 4:
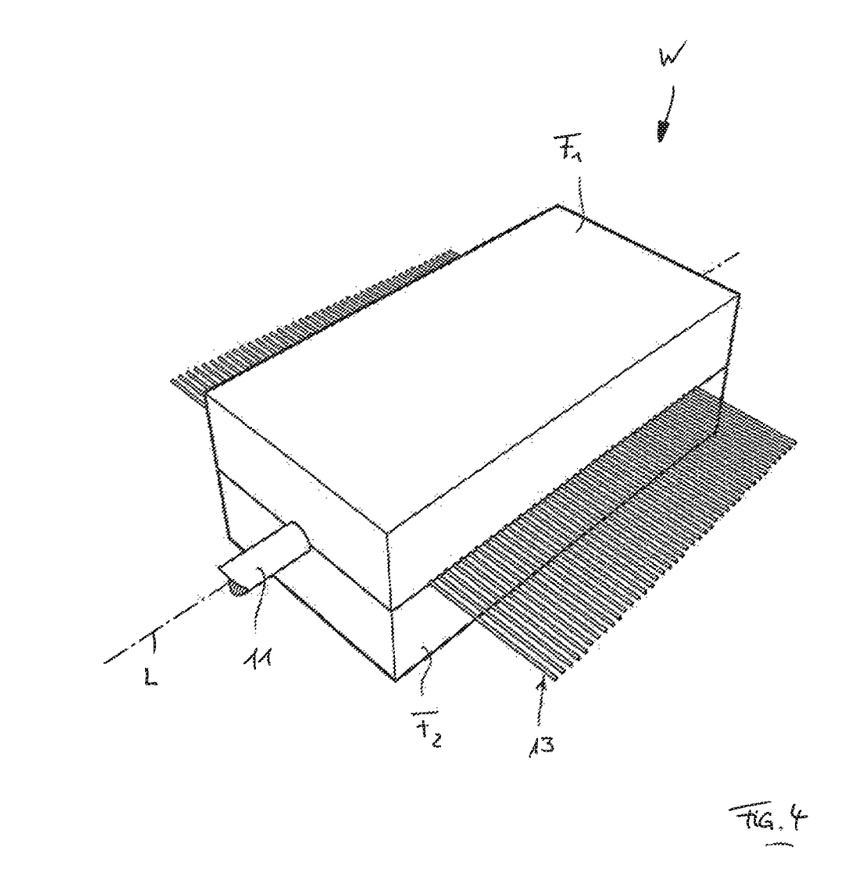
FIG. 4 is a view showing the injection mold according to FIG. 3 after closing the mold.

According to FIG. 3, a section of the prefabricated rod-shaped carrier 11 is placed together with an array of bristles 13 into the cavity $K_2$ of the lower mold half $F_2$, said bristles 13 extending essentially at right angles to the longitudinal direction L of the carrier 11 and protruding on two opposite sides beyond the cavity $K_2$. The injection mold $W_1$ is then closed by lowering the upper mold half $F_1$ onto the lower mold half $F_2$, as this is indicated by the arrows $S_1$ in FIG. 3. After closing the injection mold $W_1$, as this is shown in FIG. 4, a liquid plastic, especially a thermoplastic elastomer, is injected into the mold cavity formed by the cavities $K_1$ and $K_2$, so that the section of the carrier 11 located in the injection mold $W_1$ is provided with the sleeve-like coating 15, which slightly tapers conically towards the front end of the interdental cleaner and carries the radially outwardly protruding fingers 14 on its outer side. Moreover, it is achieved by the injected plastic forming the coating 15 that the bristles 13 will be embedded in the coating 15 and fixed in same.

Figures 5, 6:
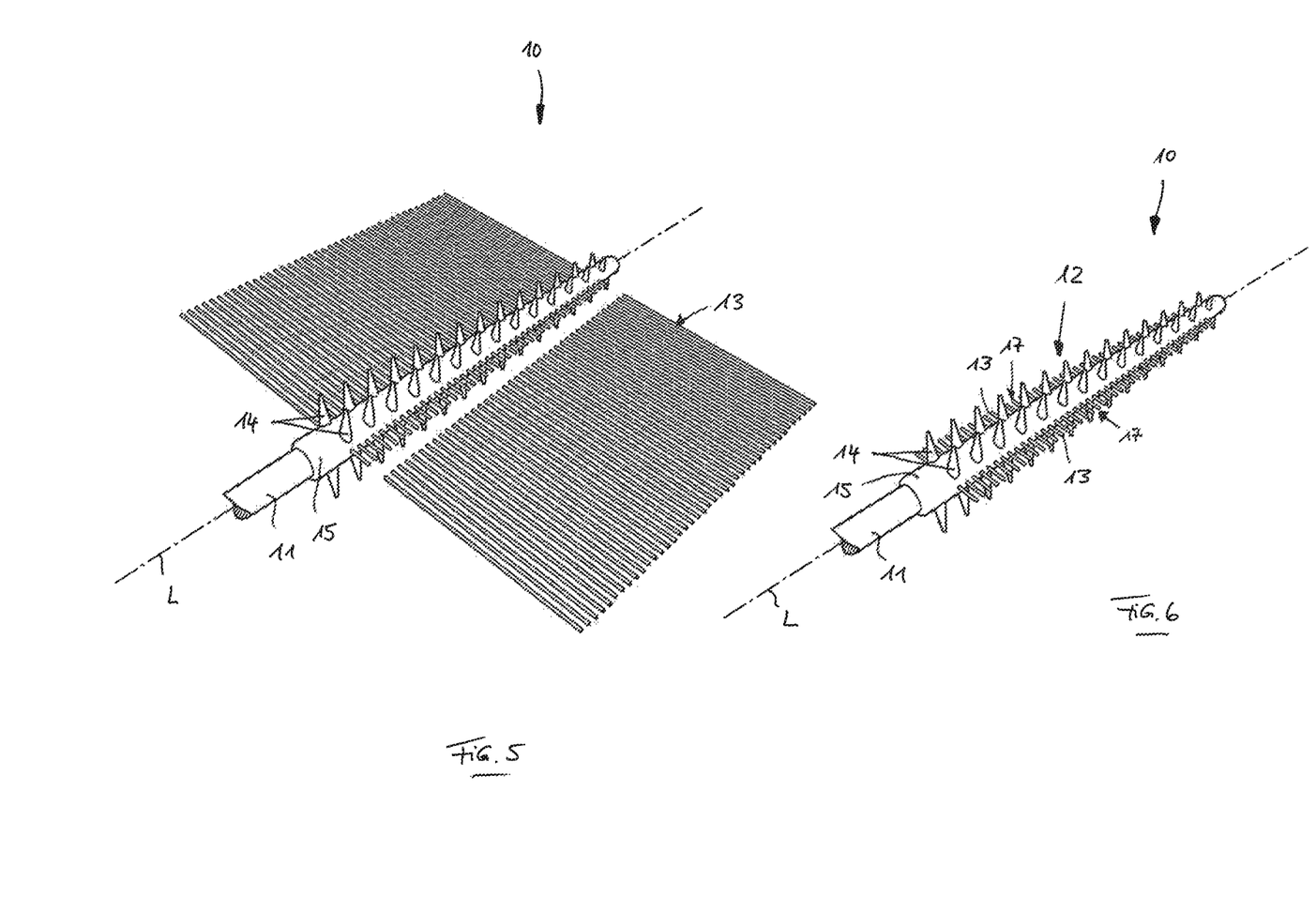
FIG. 5 is an interdental cleaner manufactured in the injection mold during the trimming of the bristles.
FIG. 6 is a view showing the interdental cleaner according to FIG. 5 after trimming the bristles.

After opening the injection mold $W_1$, the radially protruding bristles 13 are cut to a desired length, as this is shown in FIG. 5. The interdental cleaner 10 shown in FIG. 6 is formed in this way. This has the conical coating 15 seated on the front end of the rod-shaped carrier 11 with radially protruding fingers 14 formed integrally in one piece and with the bristles 13 protruding radially towards opposite sides, said bristles 13 being aligned in two linear rows 17 extending each in the longitudinal direction of the rod-shaped carrier 11.

As an alternative, the bristles may also be cut in the still closed mold or during the opening of the mold or with the mold opened or even outside the mold in a separate cutting station.

In a subsequent method step, the interdental cleaner is clamped in axially spaced sections in a first holding device 20 and a second holding device 21. The first holding device 20 has a lower clamping jaw 20.1 and an upper clamping jaw 20.2, which can clamp the interdental cleaner at the rear end of the coating 15 facing the grip part 18.

Figures 7, 8:
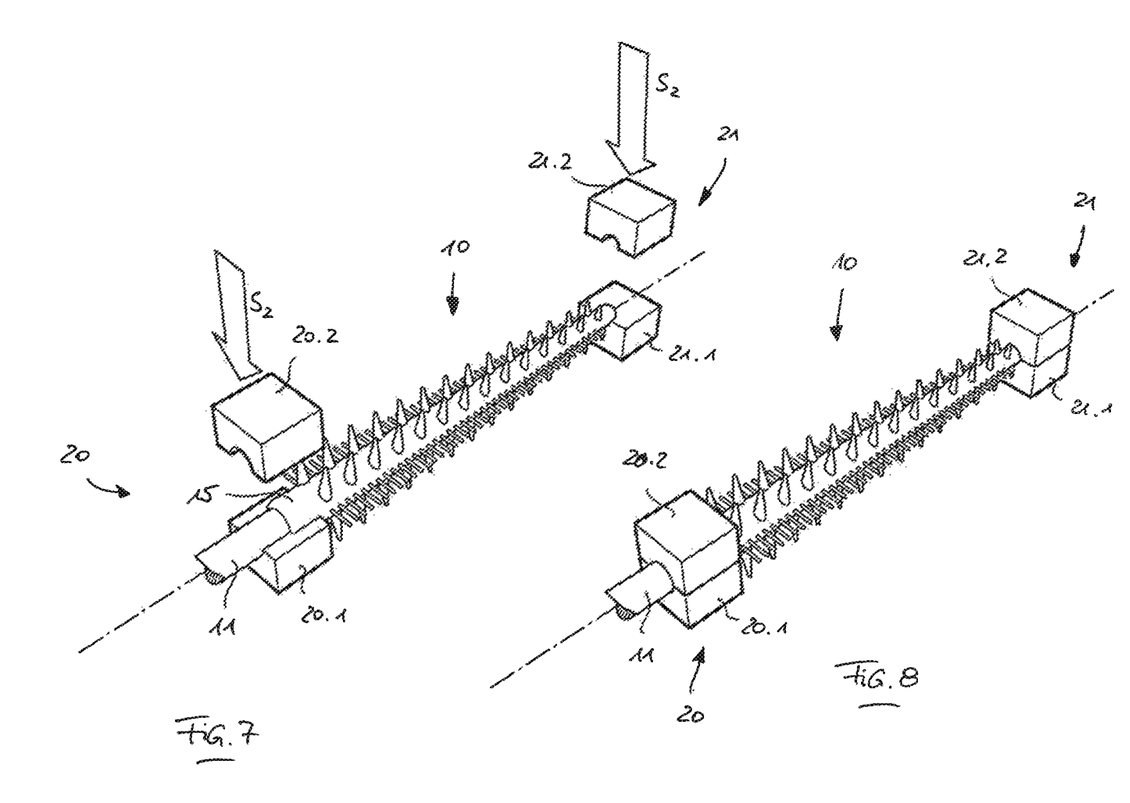
FIG. 7 is a view showing the interdental cleaner according to FIG. 6 immediately before closing the holding devices.
FIG. 8 is a view showing the interdental cleaner according to FIG. 7 after closing the holding devices.

The second holding device 21 has a lower clamping jaw 21.1 and an upper clamping jaw 21 and can clamp the interdental cleaner at the front end of the coating 15 facing away from the grip part 18. As is shown in FIG. 7, the interdental cleaner is placed into the lower clamping jaws 20.1 and 21.1, after which the upper clamping jaws 20.2 and 21.2 are moved (see arrows $S_2$) that the interdental cleaner is clamped between the first holding device 20 and the second holding device 21, as is shown in FIG. 8.

Figure 9:
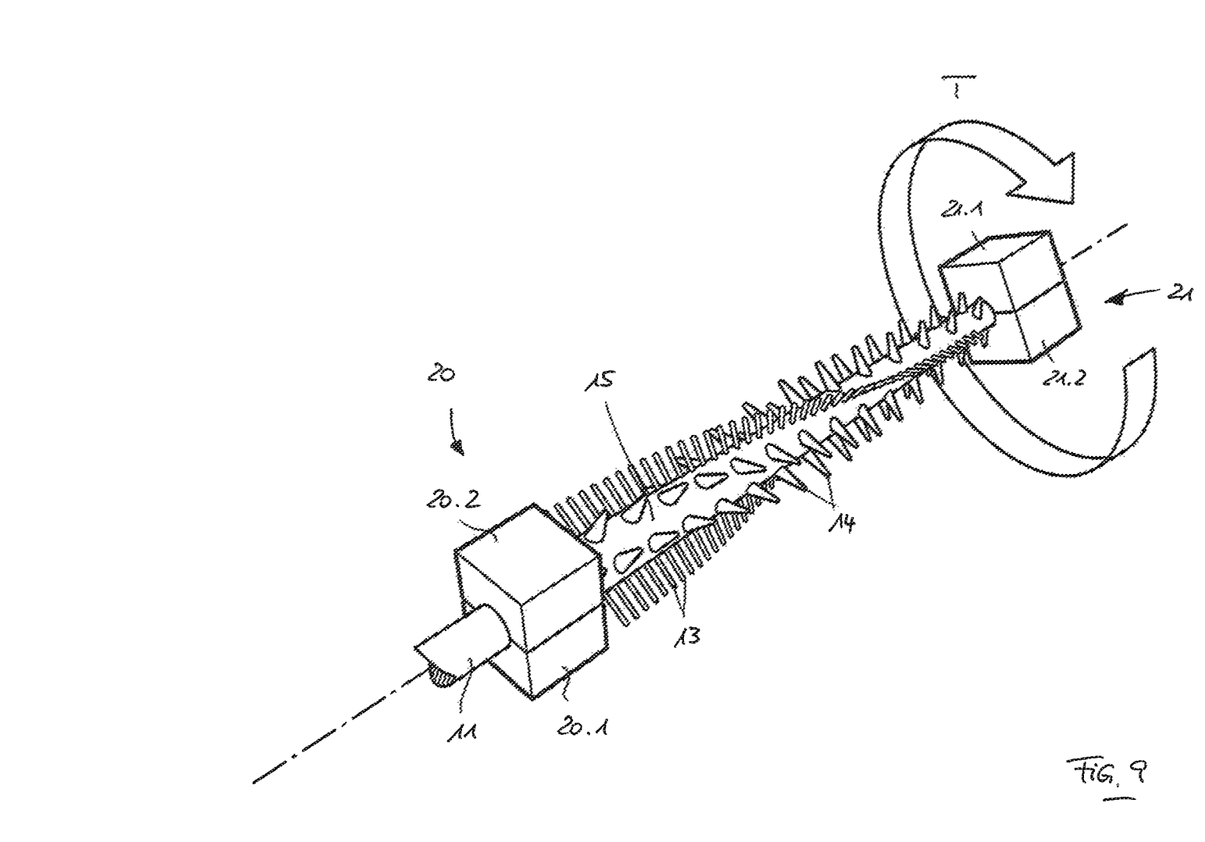
FIG. 9 is a view showing the interdental cleaner according to FIG. 8 during the twisting.

In a next method step, the front, second holding device 21 is rotated about the longitudinal axis L of the interdental cleaner 10 or rod-shaped carrier 11, as is indicated by arrow T in FIG. 9. This causes the area of the interdental cleaner 10 located between the two holding devices 20 and 21, i.e., the section of the carrier 11 located there, the coating 15 with the fingers 14 and the bristles 13 to be twisted about the longitudinal axis L of the carrier 11, so that they undergo a plastic deformation.

After opening and removing the two holding devices 20 and 21, the interdental cleaner 10 has the shape shown in FIG. 1, the carrier 11 and the coating 15 with the structuring 12 being twisted such that the fingers 14 and especially the rows 17 of bristles 13 extend helically around the carrier 11.

Figures 10, 11:
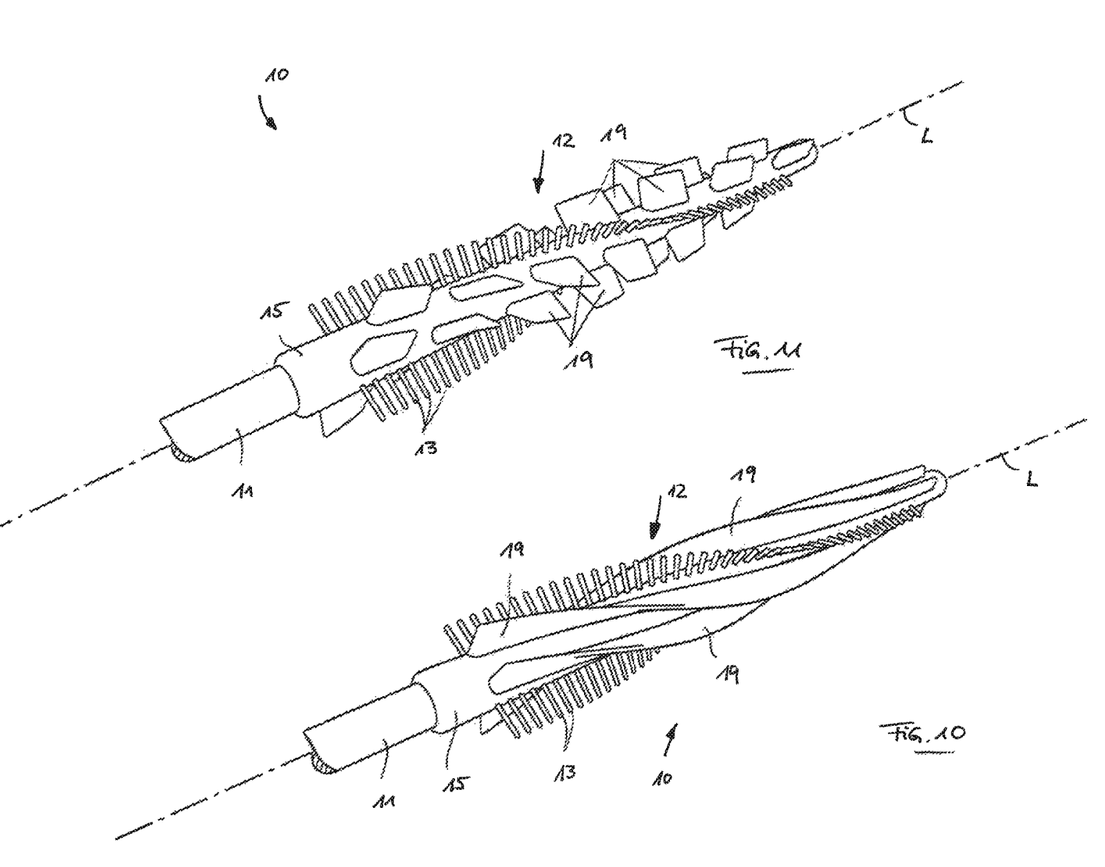
FIG. 10 is a view showing the interdental cleaner with an alternative embodiment of the structuring.
FIG. 11 is a view showing the interdental cleaner with another alternative embodiment of the structuring.

FIG. 10 shows a perspective view of the front section of the interdental cleaner 10 according to the present invention, wherein the structuring 12 has, in addition to the bristles 13, plurality of lips 19 here, which extend in the longitudinal direction of the interdental cleaner 10 and extend helically around the interdental cleaner due to the twisting of the carrier 11 and of the coating 15. The lips 19 are made integrally in one piece with the coating 15 and are distributed over the circumference of the interdental cleaner 10.

While four lips 19, which extend each approximately over the entire length of the coating 15, are arranged in the embodiment according to FIG. 10, a plurality of substantially shorter lips 19 are provided in the exemplary embodiment according to FIG. 11. The lips 19 are arranged in a plurality of longitudinal rows and helically extend round the interdental cleaner 10 because of the twisting.

Figure 12:
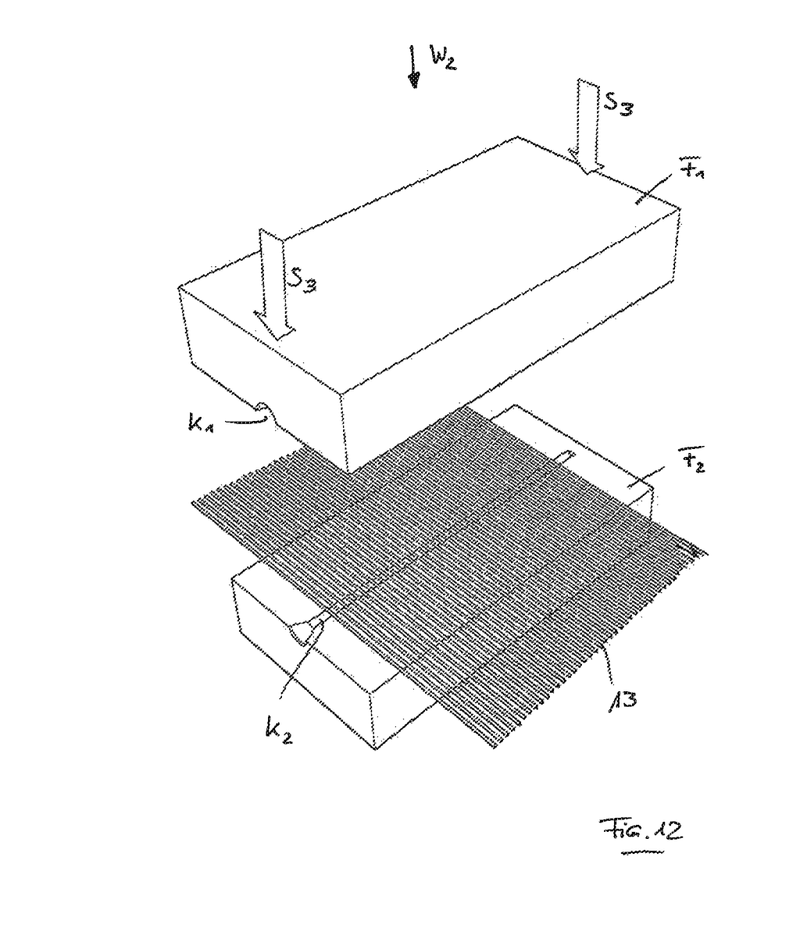
FIG. 12 is a perspective view of an opened injection mold with bristles inserted.
Figure 13:
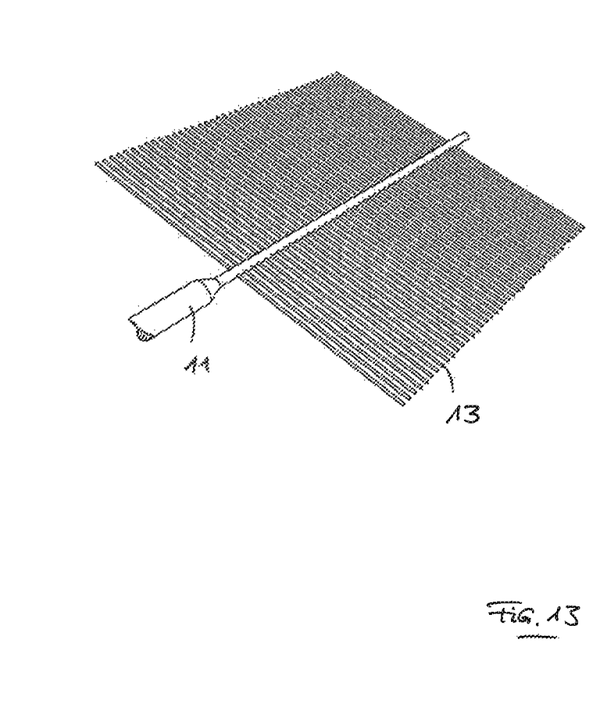
FIG. 13 is a rod-shaped carrier manufactured in the injection mold according to FIG. 12 with embedded bristles.

FIGS. 12 through 16 show an alternative method for manufacturing the interdental cleaner 10 according to the present invention. FIG. 12 shows a schematic view of an opened injection mold $W_2$ with an upper mold half $F_1$, which has an upper cavity $K_1$, and with a lower mold half $F_2$, which has a lower cavity $K_2$. An array of bristles 13 aligned parallel is inserted between the mold halves $F_1$, $F_2$, the bristles 13 extending at right angles to the longitudinal direction of the cavities $K_1$ and $K_2$, which correspond to the shape of the rod-shaped carrier to be formed. After insertion of the bristles 13, the injection mold $W_2$ is closed, as it is indicated by the arrows $S_3$ in FIG. 12. A liquid plastic, which forms the carrier 11, is injected into the mold cavity formed by the cavities $K_1$ and $K_2$ after closing the injection mold $W_2$, the bristles 13 being embedded in the carrier 11 and fixed in same, as it is shown in FIG. 13.

Figure 14:
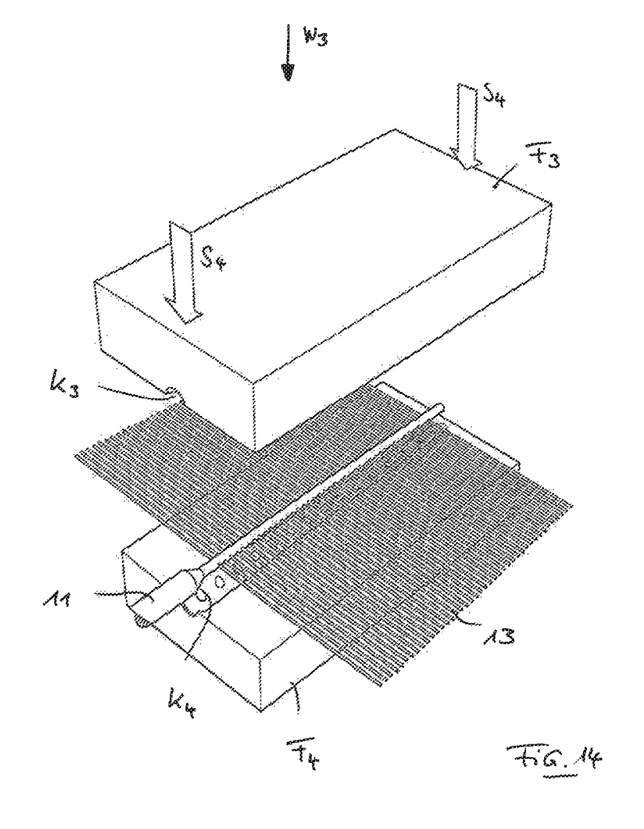
FIG. 14 is a perspective view of an opened injection mold with inserted, prefabricated carrier.
Figures 15, 16:
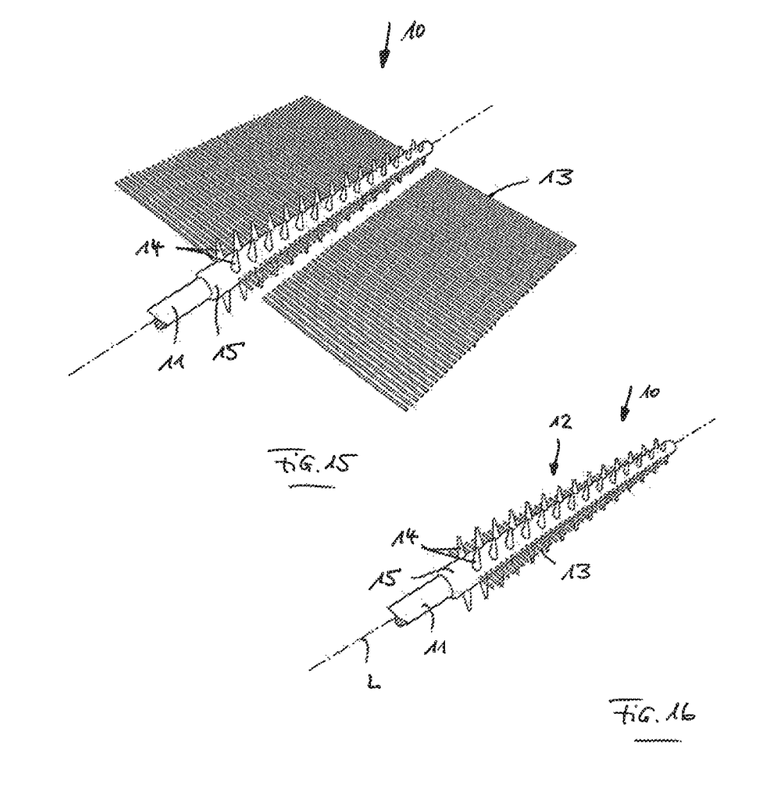
FIG. 15 is an interdental cleaner manufactured in the injection mold according to FIG. 14 during the trimming of the bristles.
FIG. 16 is a view showing the interdental cleaner according to FIG. 15 after trimming the bristles.

After opening the injection mold, the carrier 11 with the embedded bristles 13 is placed into another injection mold $W_2$, shown in FIG. 14, whose mold halves $F_3$ and $F_4$ have a respective cavity $K_3$ and $K_4$ for forming the coating 15. The carrier 11 provided with the bristles 13 is placed between the mold halves $F_3$ and $F_4$, after which the injection mold is closed, as it is indicated by the arrows S4 in FIG. 14. A plastic is subsequently injected into the cavities, so that the section of the carrier 11 located in the injection mold will be provided with the sleeve-like coating 15. The above-mentioned, radially outwardly protruding fingers 14 are formed integrally on the outer side of the coating 15. The bristles 13, which are embedded in the carrier 11, are thus also embedded in the coating 15 and are additionally held in same. After opening the injection mold, the radially protruding bristles 13 are cut to a desired length, as it is shown in FIG. 15. The interdental cleaner shown in FIG. 16, which is twisted in a subsequent method step, as is already explained on the basis of FIGS. 7 through 9, is obtained as a result.

FIG. 17 shows an alternative, simplified embodiment of an interdental cleaner 10 according to the present invention, of which only the front end is shown, because the interdental cleaner otherwise corresponds to the interdental cleaner already shown in FIG. 1. The interdental cleaner 10 has a rod-shaped carrier 11 consisting of a dimensionally stable first plastic material, in which a structuring 12 is embedded. The structuring 12 is formed by the bristles 13, which are embedded in the carrier 11 and pass through this in the radial direction, so that the bristles 13 radially protrude from the carrier 11 and extend in two rows 17 in the longitudinal direction of the carrier 11 and extend helically around the carrier 11. The two bristle rows 17 are arranged each diametrically opposite on the carrier 11, and they are coiled in the longitudinal direction of the carrier 11 by about 180° in the exemplary embodiment being shown.

The interdental cleaner 10 shown in FIG. 17 can be manufactured, for example, by an array of bristles being placed in the above-described manner into an injection mold and extrusion-coated with the plastic material of the carrier 11 in an injection mold. The carrier is subsequently twisted together with the structuring 12 about its longitudinal axis, as it was explained on the basis of FIGS. 7 through 9.

A further developed procedure for twisting the carrier 11 and the structuring 12 will be described below on the basis of FIGS. 18 through 23. It should be noted that this further developed procedure may also be used for all interdental cleaners that were described in the exemplary embodiments described so far, i.e., which additionally have a sleeve-like coating 15 and optionally also integrally formed fingers 14 and/or lips 9 protruding radially therefrom.

Figure 18:
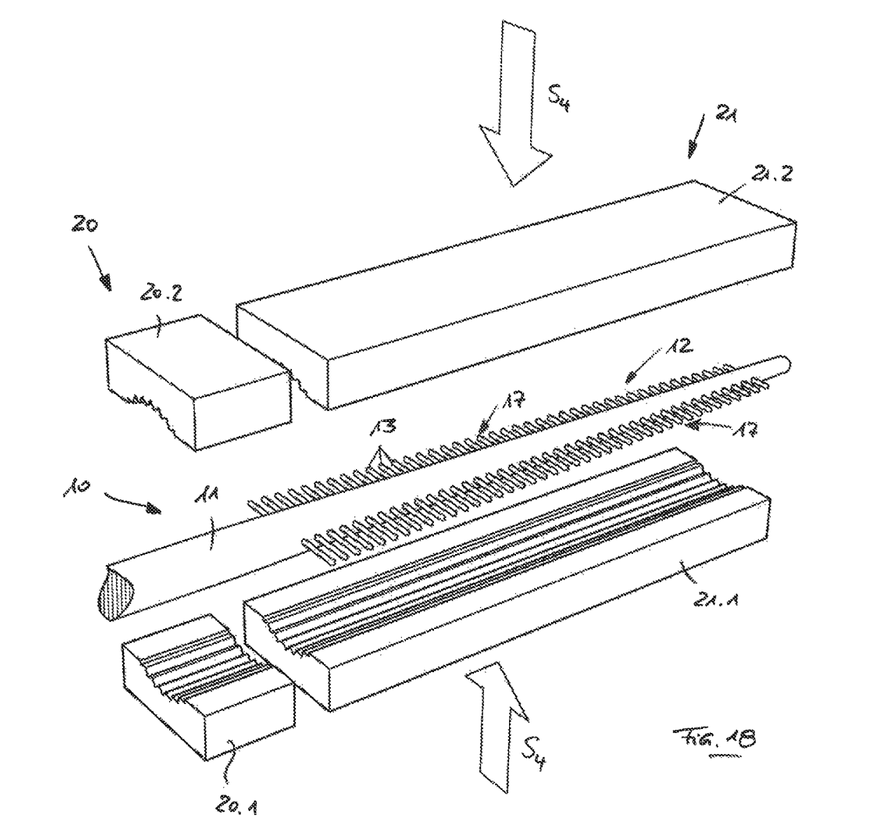
FIG. 18 is a view showing the first phase of a further development of the method for twisting the interdental cleaner.

Before twisting, the interdental cleaner 10 has a linearly aligned configuration, as it is shown in FIG. 18. Radially extending bristles 13, which protrude on both sides of the carrier 11 and form two axially extending, straight bristle rows 17 in this way, pass through the axially extending carrier 11.

A first holding device 20 has, in the aforementioned manner, a lower clamping jaw 20.1 and an upper clamping jaw 20.2, which can clamp the interdental cleaner 10 at the rear end of the structuring facing the grip part, not shown, at a spaced location from said structuring.

A second holding device 21 has a lower clamping jaw 21.1 and an upper clamping jaw 21.2. The clamping jaws are dimensioned such that they can clamp the carrier 11 between them over approximately the entire length of the structuring.

Figure 19:
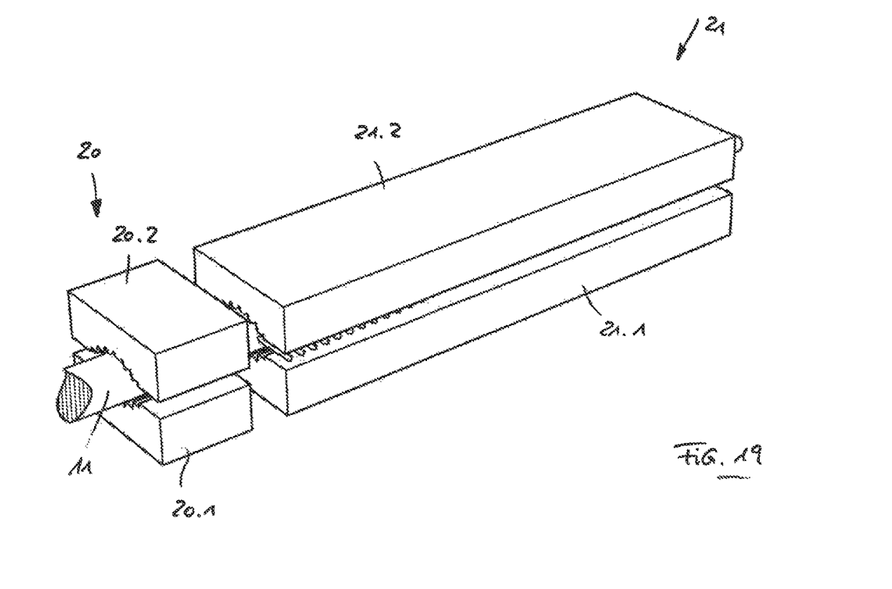
FIG. 19 is a second phase of the further developed method.

The prefabricated, not yet twisted interdental cleaner 10 is placed according to FIG. 18 between the respective lower clamping jaws 20.1, 21.1 and the upper clamping jaws 20.2 and 21.2, after which the clamping jaws are moved and closed (see arrows S4) such that the interdental cleaner 10 is claimed between the first holding device 20 and the second holding device 21, as is shown in FIG. 19. The first holding device 20 holds the carrier clamped away from the structuring 12, while the second holding device 21 clamps the carrier 121 in the entire area of the structuring 12 in the exemplary embodiment being shown.

Figure 20:
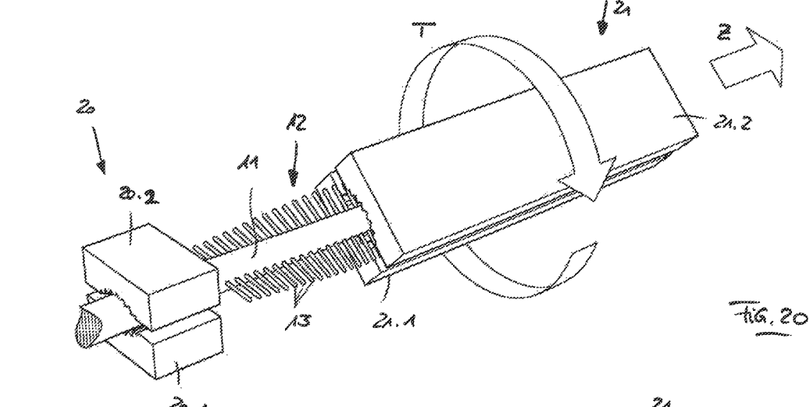
FIG. 20 is a third phase of the further developed method.

In a next method step, the second holding device 21 is rotated about the longitudinal axis L of the interdental cleaner 10 or rod-shaped carrier 11, as it is indicated by the arrow T in FIG. 20. At the same time, the second holding device is displaced in the axial direction of the carrier 11 (see arrow Z), so that the distance between the two holding devices 20, 21 is increased. As a consequence of the twisting of the second holding device 21 relative to the first holding device 20, the area of the interdental cleaner 10 located between the two holding devices 20 and 21, i.e., the section of the carrier 11 located there with the bristles 13 arranged in this area, is twisted about the longitudinal axis of the carrier, so that they undergo a deformation. The length of the area of the carrier arranged between the holding devices, which area is twisted, changes continuously because of the axial displacement of the second holding device 21 relative to the first holding device 20. It can be avoided in this way that the holding forces and the torsional forces as a consequence of the second holding device 21 are always introduced at the same axial point of the carrier.

The holding or clamping force of the second holding device 21 and the tensile force exerted by the second holding device 21 on the carrier 11 as a consequence of the axial displacement of the latter is dimensioned such that this force will not lead to an irreversible plastic stretching of the carrier 11.

Figure 21:
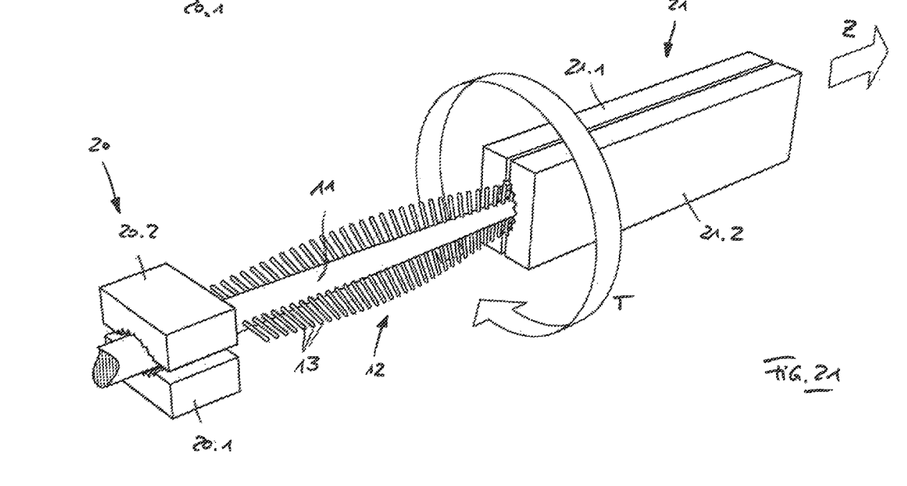
FIG. 21 is a fourth phase of the further developed method.

FIG. 20 shows a state in which the second holding device 21 is twisted relative to the first holding device 20 by about 45° and is axially displaced relative to this by a first section. FIG. 21 shows a state in which a further axial displacement of the second holding device 21 relative to the stationary first holding device 20 has taken place, so that the distance between the holding devices has increased, and in which the second holding device 21 is twisted by about 90° relative to the first holding device.

Figures 22, 23:
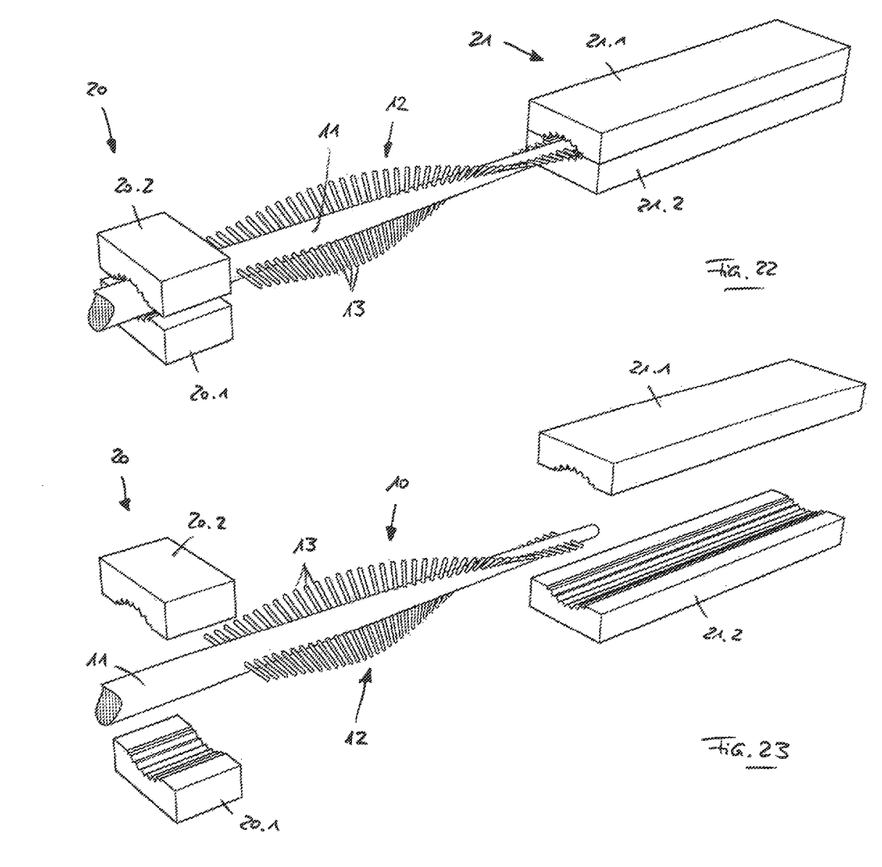
FIG. 22 is a fifth phase of the further developed method.
FIG. 23 is a sixth phase of the further developed method.

The twisting and the axial displacement of the second holding device 21 relative to the first holding device 20 is continued until the end position shown in FIG. 22 is reached, in which the distance between the two holding devices 20 and 21 is so great that the entire structuring 12 is located freely between the holding devices 20 and 21, the second holding device 21 being rotated relative to the first holding device by 180°. The holding devices are subsequently opened (see FIG. 23), as a result of which the interdental cleaner 10 is released from the holding devices 20 and 21 and has the twisted shape shown in FIG. 17.

It should be noted that the interdental cleaner usually springs back to a small amount against the direction of twisting after opening the holding devices as a consequence of internal stresses, which is not shown in this exemplary embodiment. This restoring effect can be taken into account by twisting the interdental cleaner beyond the extent desired per se, for example, 180°, so that exactly the desired amount of twisting is reached after the spring back.

While specific embodiments of the invention have been shown and described in detail to illustrate the application of the principles of the invention, it will be understood that the invention may be embodied otherwise without departing from such principles.

The invention claimed is:

1. A method for manufacturing an interdental cleaner, the method comprising the steps of:
a rod-shaped carrier formed of plastic and provided with a carrier section having a structuring with structural elements protruding radially from the carrier on at least one section of an axial length;
twisting the carrier together with the structuring about a carrier longitudinal axis (L) in at least one part of the carrier section having the structuring;
grasping the carrier, with holding devices, in two areas located at axially spaced locations from one another;
twisting the holding devices relative to one another with the carrier grasped by the holding devices; and
changing a mutual distance between the holding devices during the twisting of the carrier.

2. A method in accordance with claim 1, wherein the mutual distance between the holding devices is changed continuously during the twisting of the carrier.

3. A method in accordance with claim 1, further comprising heating the carrier before the twisting or during the twisting or both before the twisting and during the twisting.

4. A method in accordance with claim 1, wherein the twisting provides a permanent torsional deformation of the carrier that leads to a twisting of the structuring over an angle of that is greater than 30°.

5. A method in accordance with claim 4, wherein the twisting provides a permanent torsional deformation of the carrier that provides a twisting of the structuring over an angle of in a range of 60° to 360°.

6. A method in accordance with claim 4, wherein the twisting provides a permanent torsional deformation of the carrier that provides a twisting of the structuring over an angle of in a range of 60° to 120°.

7. A method in accordance with claim 4, wherein the twisting provides a permanent torsional deformation of the carrier that provides a twisting of the structuring over an angle of in a range of 90°±20°.

8. A method in accordance with claim 1, wherein the carrier is provided with a sleeved coating in an area of the structuring.

9. A method in accordance with claim 8, wherein the structuring has radially protruding fingers or radially protruding lips or both radially protruding fingers and radially protruding lips, which are made integrally in one piece with the coating.

10. A method in accordance with claim 8, wherein the structuring has radially protruding bristles, which are embedded in the carrier or in the coating or are embedded in both the carrier and in the coating.

11. A method in accordance with claim 10, wherein the bristles are positioned, located in one plane together with the carrier, in an injection mold, extrusion-coated in this while the coating is formed, and are subsequently cut to a desired length.

12. A method in accordance with claim 11, wherein the bristles, located in one plane, are extrusion-coated in an injection mold while the carrier is formed, and the bristles are cut to a desired length in a subsequent method step.

13. A method in accordance with claim 8, wherein the carrier is twisted together with the coating and with the bristles and/or with the fingers and/or the lips (19).

* * * * *